(12) United States Patent
Hassler, Jr.

(10) Patent No.: US 7,390,294 B2
(45) Date of Patent: Jun. 24, 2008

(54) PIEZO ELECTRICALLY DRIVEN BELLOWS INFUSER FOR HYDRAULICALLY CONTROLLING AN ADJUSTABLE GASTRIC BAND

(75) Inventor: William L. Hassler, Jr., Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 415 days.

(21) Appl. No.: 10/857,762

(22) Filed: May 28, 2004

(65) Prior Publication Data

US 2005/0267406 A1    Dec. 1, 2005

(51) Int. Cl.
*A61F 2/00*        (2006.01)
(52) U.S. Cl. ............................................. 600/37
(58) Field of Classification Search ............. 600/37, 600/29–32; 607/60–61, 33; 623/23.65, 23.66, 623/23.67; 128/887; 417/413.2
See application file for complete search history.

(56) References Cited

U.S. PATENT DOCUMENTS

| | | | |
|---|---|---|---|
| 4,581,018 A | 4/1986 | Jassawalla et al. | |
| 4,731,076 A | 3/1988 | Noon et al. | |
| 5,041,132 A | 8/1991 | Miyata | |
| 5,507,737 A | 4/1996 | Palmskog | |
| 5,715,837 A | 2/1998 | Chen | |
| 5,733,313 A | 3/1998 | Barreras, Sr. et al. | |
| 5,974,873 A | 11/1999 | Nelson | |
| 6,058,330 A | 5/2000 | Borza | |
| 6,102,678 A | 8/2000 | Peclat | |
| 6,162,238 A * | 12/2000 | Kaplan et al. | ............... 606/201 |
| 6,315,769 B1 | 11/2001 | Peer et al. | |
| 6,327,504 B1 | 12/2001 | Dolgin et al. | |
| 6,366,817 B1 | 4/2002 | Kung | |
| 6,430,444 B1 | 8/2002 | Borza | |
| 6,463,329 B1 | 10/2002 | Goedeke | |
| 6,482,177 B1 | 11/2002 | Leinders | |
| 6,542,350 B1 | 4/2003 | Rogers | |
| 6,592,620 B1 * | 7/2003 | Lancisi et al. | ............... 623/3.27 |
| 7,086,309 B2 * | 8/2006 | Stoianovici et al. | ........... 74/640 |
| 2003/0105385 A1 | 6/2003 | Forsell | |
| 2004/0202558 A1 * | 10/2004 | Fong et al. | ............... 417/413.2 |
| 2004/0242956 A1 * | 12/2004 | Scorvo | ....................... 600/30 |
| 2006/0127246 A1 * | 6/2006 | Forsell | ...................... 417/412 |

FOREIGN PATENT DOCUMENTS

WO    WO 00 72899    12/2000

OTHER PUBLICATIONS

EPO Search Report for Application No. 05253303.1, dated Oct. 4, 2005.

* cited by examiner

*Primary Examiner*—Charles A. Marmor, II
*Assistant Examiner*—Christine D Hopkins
(74) *Attorney, Agent, or Firm*—Frost Brown Todd. LLC

(57) ABSTRACT

A remotely controlled gastric band system that is practically immune to external magnetic fields, such as from a Magnetic Resonance Imaging (MRI) machine, incorporates a bi-directional pump and fluid reservoir to adjust fluid volume in a gastric band. A piezoelectrically driven (e.g., rotary actuator, linear actuator) selectively compresses and expands a metal bellows hermetically sealed within a biocompatible and non-ferromagnetic case such as titanium.

6 Claims, 10 Drawing Sheets

PIEZO ELECTRICALLY DRIVEN BELLOWS INFUSER FOR HYDRAULICALLY CONTROLLING AN ADJUSTABLE GASTRIC BAND

CROSS REFERENCE TO RELATED APPLICATIONS

The present application is related to three co-pending and commonly-owned applications filed on even date herewith, the disclosure of each being hereby incorporated by reference in their entirety, entitled respectively:

"METAL BELLOWS POSITION FEED BACK FOR HYDRAULIC CONTROL OF AN ADJUSTABLE GASTRIC BAND" to William L. Hassler, Jr., Daniel F. Dlugos, Jr., Rocco Crivelli, Ser. No. 10/856,97122;

"THERMODYNAMICALLY DRIVEN REVERSIBLE INFUSER PUMP FOR USE AS A REMOTELY CONTROLLED GASTRIC BAND" to William L. Hassler, Jr., Daniel F. Dlugos, Jr., Ser. No. 10/857,315; and "BI-DIRECTIONAL INFUSER PUMP WITH VOLUME BRAKING FOR HYDRAULICALLY CONTROLLING AN ADJUSTABLE GASTRIC BAND" to William L. Hassler, Jr., Daniel F. Dlugos, Jr., Ser. No. 10/857,763.

FIELD OF THE INVENTION

The present invention relates, in general, to medically implantable reversible pumps, and more particularly, to such pumps that are suitable for long term use without fluid loss such as for hydraulically controlling an artificial sphincter.

BACKGROUND OF THE INVENTION

Since the early 1980s, adjustable gastric bands have provided an effective alternative to gastric bypass and other irreversible surgical weight loss treatments for the morbidly obese. The gastric band is wrapped around an upper portion of the patient's stomach, forming a stoma that restricts food passing from an upper portion to a lower portion of the stomach. When the stoma is of the appropriate size, food held in the upper portion of the stomach provides a feeling of fullness that discourages overeating. However, initial maladjustment or a change in the stomach over time may lead to a stoma of an inappropriate size, warranting an adjustment of the gastric band. Otherwise, the patient may suffer vomiting attacks and discomfort when the stoma is too small to reasonably pass food. At the other extreme, the stoma may be too large and thus fail to slow food moving from the upper portion of the stomach, defeating the purpose altogether for the gastric band.

In addition to a latched position to set the outer diameter of the gastric band, adjustability of gastric bands is generally achieved with an inwardly directed inflatable balloon, similar to a blood pressure cuff, into which fluid, such as saline, is injected through a fluid injection port to achieve a desired diameter. Since adjustable gastric bands may remain in the patient for long periods of time, the fluid injection port is typically installed subcutaneously to avoid infection, for instance in front of the sternum or over the fascia covering one of the oblique muscles. Adjusting the amount of fluid in the adjustable gastric band is achieved by inserting a Huber tip needle through the skin into a silicon septum of the injection port. Once the needle is removed, the septum seals against the hole by virtue of compressive load generated by the septum. A flexible catheter communicates between the injection port and the adjustable gastric band.

While the injection port has been successfully used to adjust gastric bands, it would be desirable to make adjustments noninvasively. Insertion of the Huber tip syringe is typically done by a surgeon, which may be inconvenient, painful, or expensive for the patient. In addition, a skin infection may occur at the site of the insertion of the syringe. Consequently, it would be desirable to remotely control an adjustable gastric band.

Infusers have been implanted in patients for controllable dispensing of a liquid drug, such as described in U.S. Pat. No. 4,581,018. A cylindrical metal bellows has a movable end that is drawn toward its nonmoving end by a lead screw that passes through the bellows into a threaded hole of the case. Thus, the volume of the metal bellows accumulator was affirmatively controlled by the number of turns made by the lead screw, avoiding inadvertent overdoses in dispensing a liquid drug.

However, infuser pumps are intended to be driven in only one direction whereas adjusting constriction of the gastric band often requires that fluid be removed from the elastomeric balloon to reduce constriction as well as the reverse direction to increase constriction.

In addition, it is becoming increasingly important that implanted devices in general be operable and nonresponsive to a strong magnetic field as the use of magnetic resonance imaging (MRI) becomes more common. An MRI machine produces a strong magnetic field, which may be up to 3.0 Teslas in flux density, that will impart a strong magnetic force upon any ferromagnetic material. Devices such as electrical motors may be damaged by such magnetic fields or the patient may feel discomfort. Moreover, ferromagnetic material may create artifacts in the radio frequency (RF) return that the MRI machine detects and processes by disturbing the magnetic field.

In an implanted peristaltic pump, such as described in U.S. Pat. No. 6,102,678, a piezoelectric drive system is used to provide a rotary device that is lightweight, compact with very small axial volume and with the particular desirable feature of being practically unaffected by external magnetic influences. While a peristaltic pump differs substantially from a bi-directional metal bellows accumulator/pump, it would be desirable to incorporate similar features of MRI compatibility in a bi-directional infuser pump.

Consequently, a significant need exists for a reversible pump suitable for medical implantation to remotely adjust a gastric band.

BRIEF SUMMARY OF THE INVENTION

The present invention addresses these and other problems in the prior art, by providing a reversible pump having no ferromagnetic materials that can provide an accurately controllable volume to a second implanted device, such as a closed gastric band. In particular, a bellows accumulator may be directly collapsed or extended to positively displace fluid accumulated therein, thereby serving as both a reversible pump and reservoir, by utilizing a piezoelectric drive system that is practically immune to external magnetic fields.

In one aspect of the invention, a bellow accumulator may be selectively collapsed or expanded between a larger and smaller volume as part of an implantable device in order to provide bidirectional fluid control of another implanted member. A piezoelectric drive effects this selective movement of the bellows accumulator, which being substantially nonresponsive to electromagnetic interferences means that the device may be rendered safe and operable even in proximity to an MRI machine.

These and other objects and advantages of the present invention shall be made apparent from the accompanying drawings and the description thereof.

BRIEF DESCRIPTION OF THE FIGURES

While the specification concludes with claims particularly pointing out and distinctly claiming the present invention, it is believed the same will be better understood by reference to the following description, taken in conjunction with the accompanying drawings in which:

DETAILED DESCRIPTION OF THE INVENTION

Figure 1:
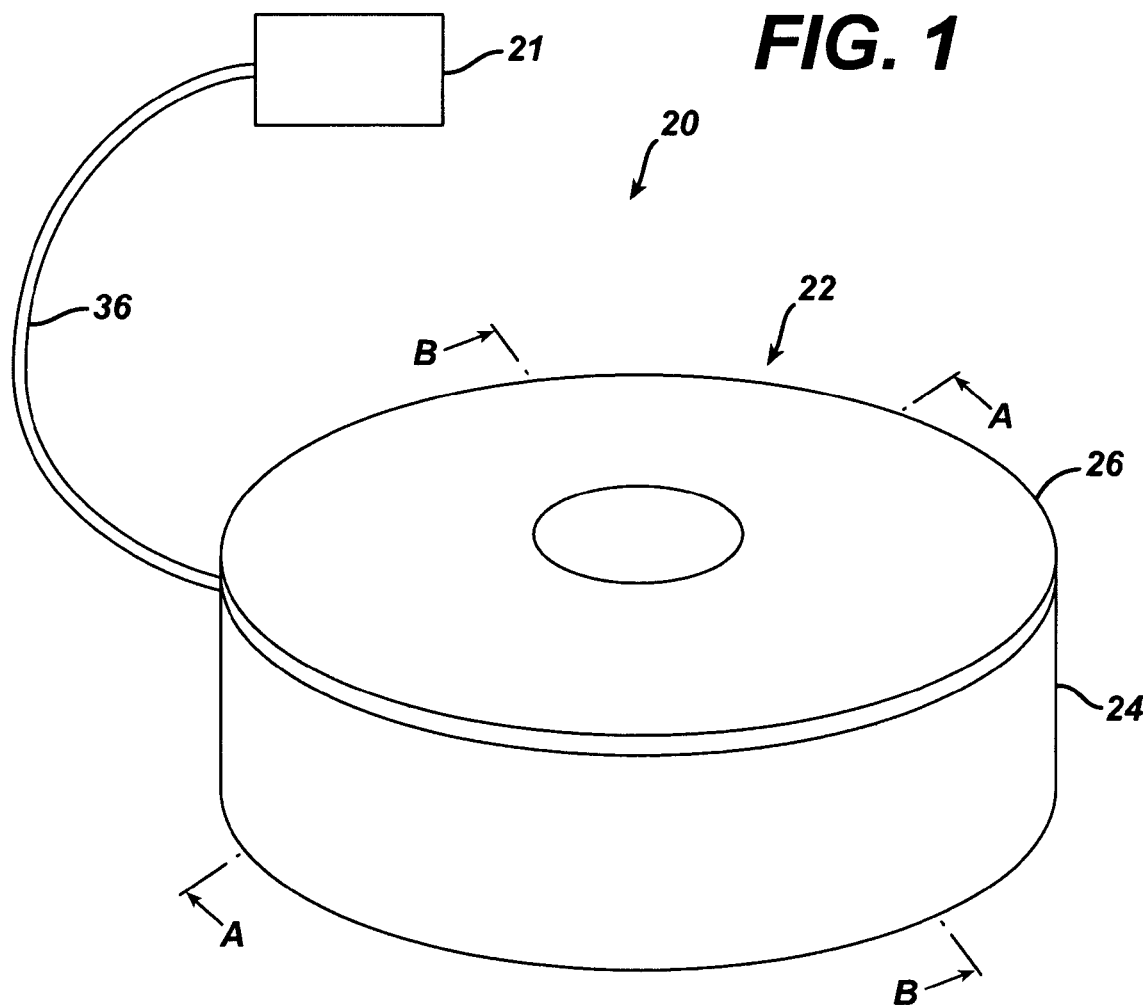
FIG. 1 is a diagrammatic view of a pump system in accordance with the present invention.

Referring now to the drawings in detail, wherein like numerals indicate the same elements throughout the views, FIG. 1 provides a diagrammatic view of an implantable pump system 20 in accordance with one embodiment of the present invention. As will be described in more detail below, pump system 20 may be implanted under a patient's skin and controlled by an active telemetry system to direct fluid flow to and from a therapeutic implant. Although the invention is described herein with specific reference to the use of the implantable pump with an artificial sphincter 21, such as an adjustable gastric band, such description is exemplary in nature, and should not be construed in a limiting sense. The implantable pump of the present invention may also be utilized in any number of different apparatuses or systems in which it is desirable to provide bi-directional fluid flow between two interconnected subcutaneous components.

As shown in FIG. 1, the pump system 20 includes an implantable pump device 22 having a generally cylindrical outer casing 24 extending around the sides and bottom portions of the pump device 22, and an annular cover 26 extending across a top portion. Annular cover 26 may be of varying thickness, with the thickest portion located at the center 30 (shown in FIG. 2) of the cover 26. Casing 24 and cover 26 may be formed of titanium or another type of appropriate, non-magnetic material, as are the other parts of pump device 22 that are exposed to body tissue and fluids. The use of titanium or a similar material prevents pump device 22 from reacting to body fluids and tissues in which the pump device 22 may be implanted.

Figure 2:
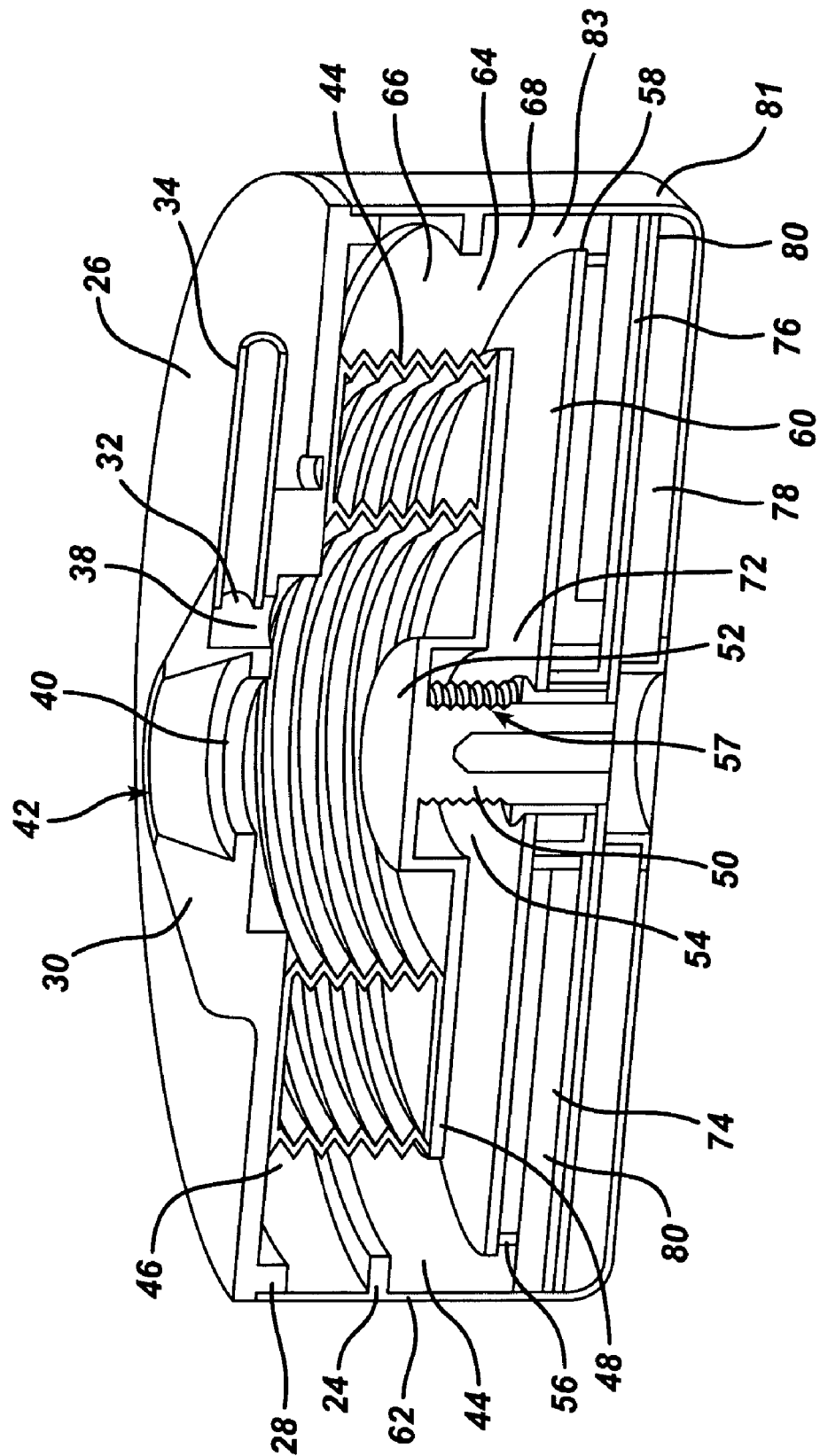
FIG. 2 is a cross-sectional view of an implantable pump of the pump system taken along line A-A of FIG. 1.
Figure 3:
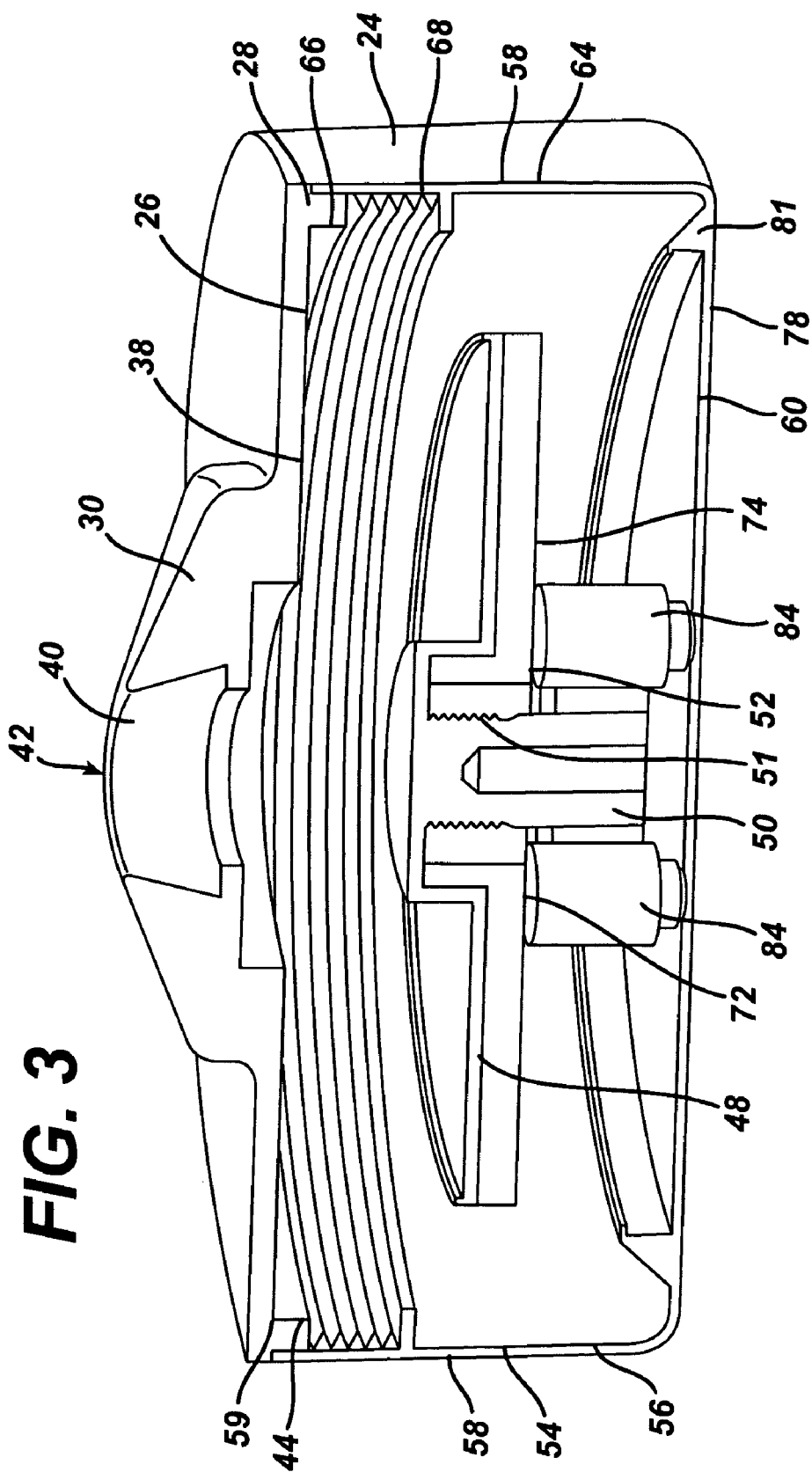
FIG. 3 is a cross-sectional view of the implantable pump taken along line B-B of FIG. 1.
Figure 4:
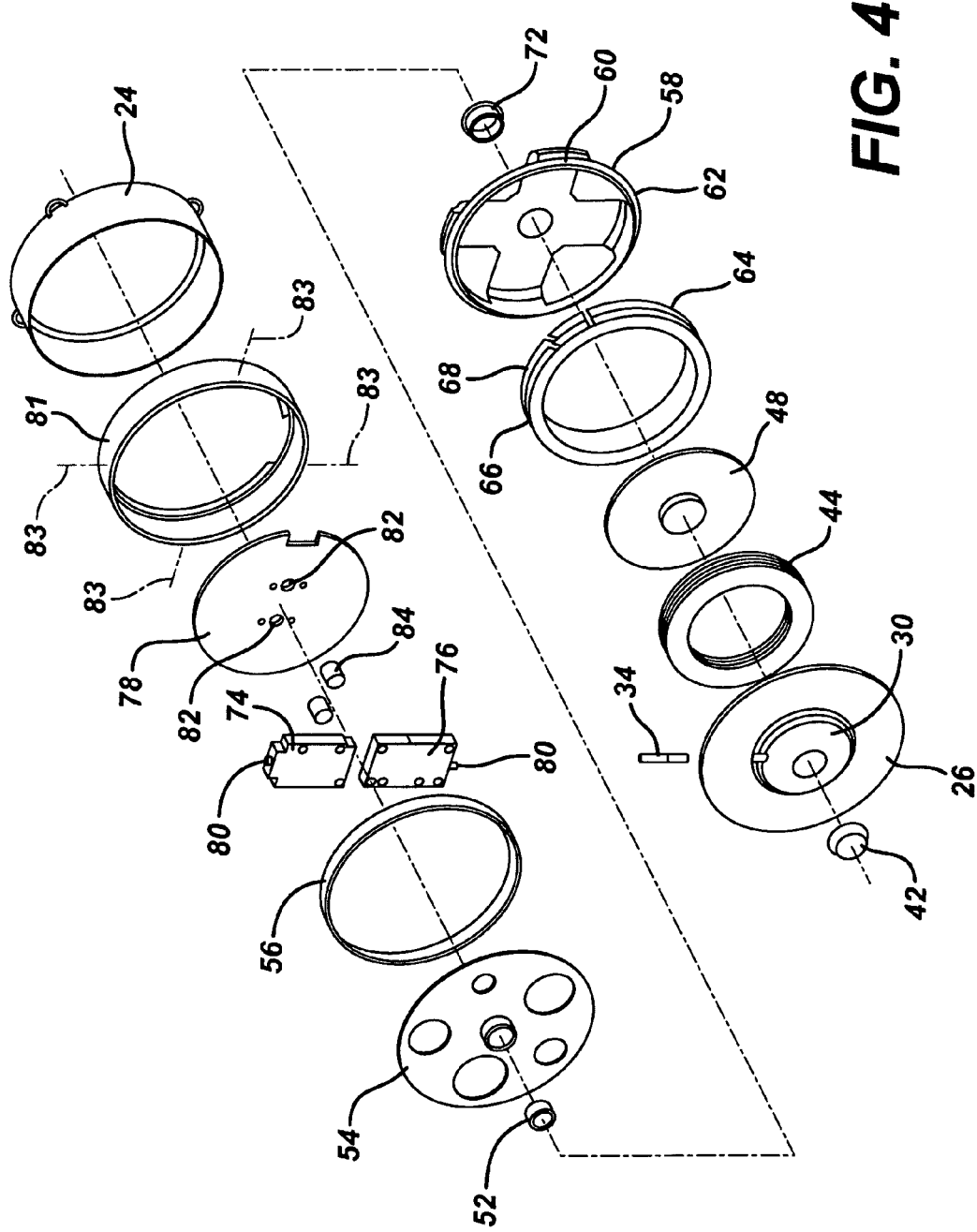
FIG. 4 is a front, exploded isometric view showing internal components of a first embodiment of the implantable pump of the present invention.
Figure 5:
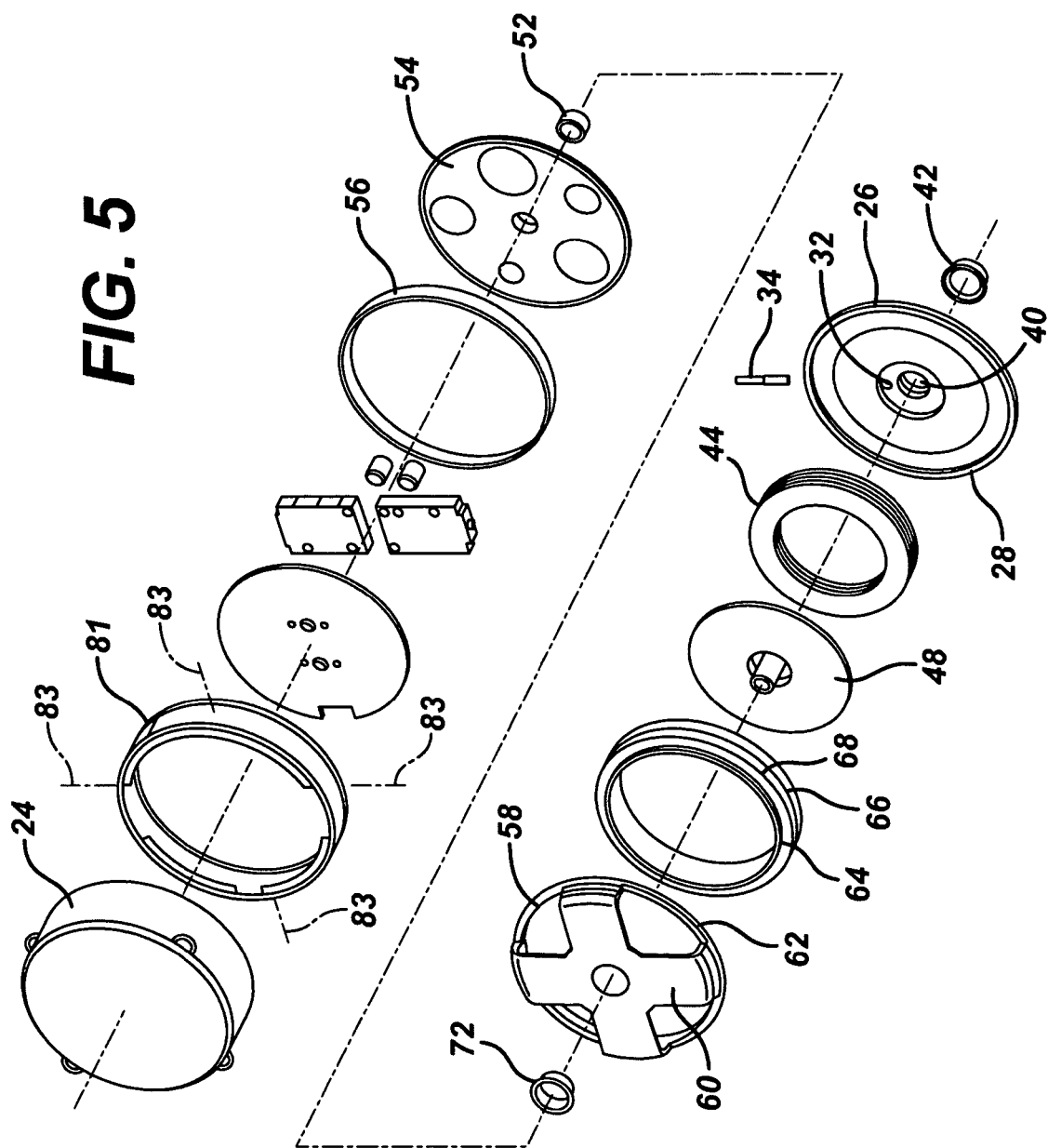
FIG. 5 is a rear, exploded isometric view showing internal components of the first embodiment of the implantable pump of FIG. 4.

FIGS. 2 and 3 are cross-sectional views showing the internal components of a first embodiment of pump device 22, with FIG. 3 being a 90° rotation of the FIG. 2 view. In addition, FIGS. 4 and 5 provide exploded isometric views from both the forward and rearward directions of pump device 22, illustrating the relative positions of the components within the pump device 22. As shown in FIGS. 2-5, thickened center portion 30 of cover 26 is molded or machined to include a duct 32. A catheter port 34 extends laterally from duct 32 in center portion 30 to connect with an external fluid-conveying device, such as, for example, a catheter 36 as shown in FIG. 1. Duct 32 connects catheter port 34 with a fluid reservoir 38 in the interior of pump device 22. Duct 32, catheter port 34 and catheter 36 combine to provide bi-directional fluid flow between fluid reservoir 38 and a secondary implant. As shown in FIGS. 1 and 2, cover 26 includes a port 40 into which a hypodermic needle (not shown) may be inserted either through the patient's skin, or prior to implantation of device 22, in order to increase or decrease the fluid volume in reservoir 38. A septum 42 is disposed in port 40 to enable infusions by a hypodermic needle while preventing other fluid transmissions through the port 40. Near the periphery of cover 26, an annular lip 28 extends downwardly in overlapping contact with casing 24. Casing 24 and cover 26 are welded together along lip 28 to form a hermetic seal.

Fluid reservoir 38 comprises a collapsible bellows 44 securely attached at a top peripheral edge 46 to cover 26. Bellows 44 are comprised of a suitable material, such as titanium, which is capable of repeated flexure at the folds of the bellows, but which is sufficiently rigid so as to be non-compliant to variations in pressure within reservoir 38. The lower peripheral edge of bellows 44 is secured to an annular bellows cap 48, which translates vertically within pump device 22. The combination of cover 26, bellows 44 and bellows cap 48 defines the volume of fluid reservoir 38. The volume in reservoir 38 may be expanded by moving bellows cap 48 in a downward direction opposite cover 26, thereby stretching the folds of bellows 44 and creating a vacuum to pull fluid into the reservoir. Similarly, the volume in reservoir 38 may be decreased by moving bellows cap 48 in an upward direction towards cover 26, thereby compressing the folds of bellows 44 and forcing fluid from the reservoir into duct 32 and out through catheter port 34.

As shown in FIGS. 2 and 3, bellows cap 48 includes an integrally formed lead screw portion 50 extending downwardly from the center of the cap 48. Lead screw portion 50 includes a screw thread, as indicated by numeral 51, that operatively engages a matching thread on a cylindrical nut 52. The mating threads 51 on lead screw portion 50 and cylindrical nut 52 enable the lead screw portion 50 to translate vertically relative to cylindrical nut 52 when the nut 52 is rotated about a longitudinal axis of the lead screw portion 50. The outer circumference of nut 52 is securely attached to an axial bore of a rotary drive plate 54. A cylindrical drive ring 56 is in turn mounted about an outer annular edge of rotary drive plate 54 to extend downwardly from the plate 54 on a side opposite to nut 52. Nut 52, drive plate 54 and drive ring 56 are all securely attached together by any suitable means, to form an assembly that rotates as a unit about the longitudinal axis formed by lead screw portion 50.

A bushing frame 58 is provided in pump device 22 and securely connected along a top edge to annular lip 28. Bushing frame 58 includes a bottom portion 60 extending beneath bellows cap 48, and a cylindrically-shaped side wall portion 62 spaced about the periphery of bellows 44. A cylindrical coil bobbin 64 extends about the inner circumference of frame 58, between the frame and bellows 44. One or more coil windings may be wound about the circumference of bobbin 64 for providing transcutaneous signal transfer between an external power and communication source and pump device 22. In the embodiment shown in FIGS. 2-5, a first coil winding 66 on bobbin 64 forms a closed loop antenna ("secondary TET coil") that is inductively coupled to a primary transcutaneous energy transfer (TET) coil in the external interface. When the primary TET coil in the external interface is energized, an RF power signal is transmitted to the secondary TET coil 66 to provide a power supply for driving pump device 22. A second coil winding 68 on bobbin 64 provides for control signal transfer between pump device 22 and an external programmable control interface. Coil winding 68 forms an antenna ("secondary telemetry antenna") that is inductively coupled to a primary telemetry antenna in the external device for transmitting RF control signals between the external interface and pump 22 at a fixed frequency. A bushing 72 is press fit into bushing frame 58 to extend between frame 58 and drive plate 54. Bushing 72 includes an axial opening for nut 52 and lead screw 50. Bushing 72 separates bushing frame 58 and drive plate 54 to allow the drive plate and nut 52 to rotate relative to lead screw 50 without interference between the bushing frame 58 and drive plate 54. In addition, bushing 72 prevents nut 52 from moving radially or axially toward cover 26.

As mentioned above, cylindrical nut 52, drive plate 54 and drive ring 56 form an assembly that translates lead screw 50 of bellows cap 48 when ring 56 is rotatably driven. In the first embodiment of the present invention, drive ring 56 is rotatably driven by one or more piezoelectric harmonic motors that utilize a series of harmonic vibrations to generate rotation in the ring. In the embodiment shown in FIGS. 2-5, a pair of harmonic motors 74, 76 are placed in frictional contact with the inner circumference of drive ring 56, so that the harmonic motion of the motors in contact with the ring produces rotation of the ring 56. Motors 74, 76 may be spaced 180° apart about the inner circumference of ring 56, beneath drive plate 54. Motors 74, 76 are mounted to a support board 78, with a tip portion 80 of each motor in frictional contact with the inner circumferential surface of drive ring 56. When motors 74, 76 are energized, tips 80 vibrate against drive ring 56, producing a "walking" motion along the inner circumference of the ring 56, thereby rotating the ring 56.

A spring (not shown) within each motor 74, 76 biases motor tip portions 80 into continuous frictional contact with ring 56 to enable precise positioning of drive ring 56, and a holding torque on the ring 56 between motor actuations to prevent position shift in the ring 56. Drive ring 56 may be manufactured from a ceramic, or other similar material, in order to provide for the required friction with motor tip portions 80 while also limiting wear on the tip portions 80.

It should be appreciated by those skilled in the art having the benefit of the present disclosure that a piezoelectric harmonic motor, or another type of harmonic motor having no intrinsic magnetic field or external magnetic field sensitivity may be used in the present invention to enable patients with the implant to safely undergo Magnetic Resonance Imaging (MRI) procedures, or other types of diagnostic procedures that rely on the use of a magnetic field. The use of a piezoelectric harmonic motor rather than an electromagnetic servomotor in the present invention enables the device to provide the same high resolution, dynamic performance of a servomotor, yet is MRI safe. An example of a suitable piezoelectric harmonic motor for the present invention is the STM Series Piezoelectric Motor produced by Nanomotion Ltd. of Yokneam, Israel. This motor is described in detail in The STM Mechanical Assembly and the Nanomotion Product/Selection Guide, both published by Nanomotion, Ltd. Other types of harmonic motors may also be utilized in the present invention without departing from the scope of the invention. Examples of these other motors include, without limitation, the Elliptec motor by Elliptec AB of Dortmund Germany, which is described in the Elliptec Resonant Actuator Technical Manual. Version 1.2; the Miniswys motor by Creaholic of Switzerland; the PDM 130 Motor by EDO Electro-Ceramic Products of Salt Lake City, Utah which is described in the technical brochure High Speed Piezoelectric Micropositioning Motor Model PDA130.; and the Piezo LEGS motor which is manufactured by PiezoMotor Uppsala AB of Uppsala, Sweden and described in the brochure entitled Linear Piezoelectric Motors by PiezoMotor Uppsala AB. Additionally, piezoelectric inchworm motors may be utilized to drive a ceramic ring or plate, which motion is then translated into movement of a bellows. Examples of suitable piezoelectric inchworm motors include the IW-800 series INCHWORM motors produced by Burleigh EXPO America of Richardson, Tex. and the TSE-820 motor produced by Burleigh Instruments, Inc of Victor, N.Y. In addition, other types of rotary friction motors, and other types of motors which rely upon piezoelectric effects to drive a member may also be used without departing from the scope of the invention.

As discussed above, each motor 74, 76 in the first embodiment is mounted to a board 78 using a plurality of screws or other type of secure attachment mechanism. While two motors are depicted in the figures, additional motors may be utilized provided the driving member of each motor is in frictional contact with the drive ring. In addition to supporting motors 74, 76, board 78 may also include control circuitry for powering and operating the motors in accordance with signals transmitted from an external device. Alternatively, a separate circuit board could be included in pump device 22 that would include the circuitry for controlling motors 74, 76. The control circuitry on board 78 is electrically connected to coil windings 66, 68 for receiving power to drive motors 74, 76, as well as receiving and transmitting control signals for pump 22. Board 78 is attached to a wire assembly sheath 81, which is in turn connected by pins 83 to bushing frame 58. The connection between board 78 and frame 58 forms a mechanical ground to prevent the board and attached motors 74, 76 from torquing within pump device 22 when the motors are energized. As shown in FIGS. 3-5, board 78 may also include one or more openings 82 for retaining plate supports 84. Supports 84 extend between motors 74, 76, from board 78 to drive plate 54, to support the drive plate 54 and constrain the plate 54 from moving axially away from bellows 44.

Figure 6:
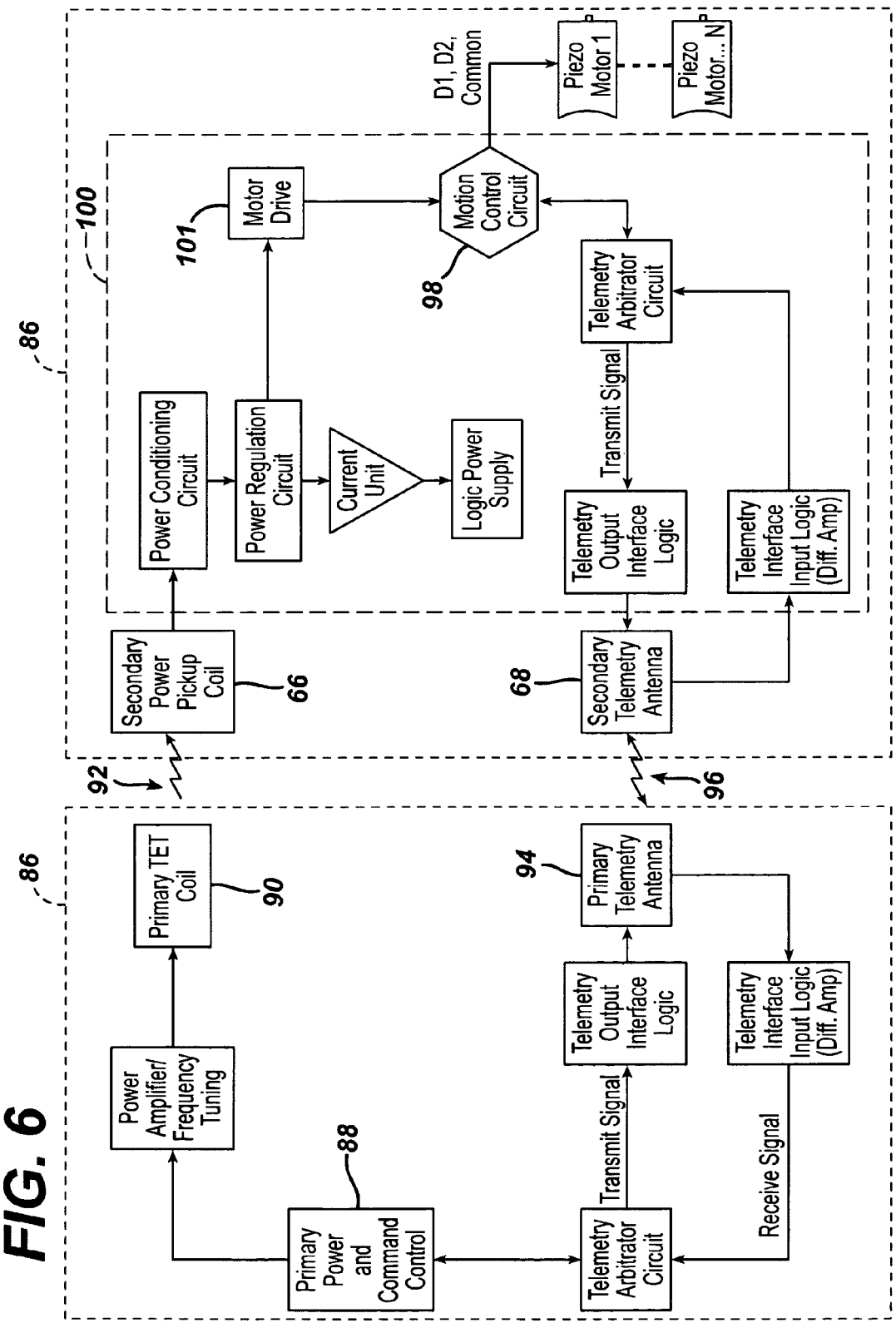
FIG. 6 is a schematic illustration in block diagram form of the power, telemetry, and control systems of the pump device.

FIG. 6 provides a schematic illustration of the TET power, telemetry and control systems of the present invention. As mentioned above, pump device 22 is driven by an active telemetry system in which the power required to drive the pump is transmitted to the pump device 22 from outside the patient's body using RF signals. Accordingly, pump device 22 may not require a battery or other type of internal power source, thereby eliminating the need to replace the power source and reducing the size of the implanted device. As shown in FIG. 6, pump device 22 is controlled by an external device 86 which includes a primary power supply and command control 88. Control 88 generates a power signal that drives a primary TET coil 90 to generate an RF power signal 92. Control 88 also transmits a data signal to communications antenna 94, which generates an RF telemetry signal 96 encoded with operating data for pump device 22. Power and communication signals 92, 96 are transmitted in different, fixed frequency bandwidths to pump device 22. When antenna coils 90, 94 of external device 86 are placed on or near the patient's skin in the vicinity of implanted pump device 22, power signal 92 from TET coil 90 induces a voltage in the pump internal secondary TET coil 66. The power signal from coil 66 is transmitted to internal control circuitry 100 on board 78. The power signal is conditioned and stepped up to a higher voltage. The signal is then used to power a motor driver 101. Similarly, telemetry signal 96 generates a voltage signal in secondary telemetry antenna 68. The signal generated in secondary telemetry antenna 68 is decoded by control circuitry 100, and the control information from the signal 96 is applied to a motion control 98. Motion control 98 interprets the control data to selectively apply power from motor driver 101 to motors 74, 76 to drive the motors 74, 76 and move bellows 44.

Motion control 98 drives motors 74, 76 by providing an appropriate electrical signal to each motor 74, 76 through a pair of electrical control lines. In the exemplary piezoelectric harmonic motor embodiment, drive ring 56 rotates in either a clockwise or counterclockwise direction depending upon which control lines are excited in the motors. Motion control 98 includes switches for directing a voltage signal amongst the different control lines. When a voltage signal is applied across a first pair of control lines, the piezoelectric element vibrates in a first mode, causing drive ring 56 to rotate in a first direction. When a voltage signal is applied to a second pair of control lines, the piezoelectric element vibrates in a second mode, causing drive ring 56 to rotate in the opposite direction. Rotation of drive ring 56 in a first direction raises bellows cap 48, thereby decreasing the volume in fluid reservoir 38 and forcing fluid from the pump into catheter 36. Similarly, rotation of drive ring 56 in a second, opposite direction lowers bellows cap 48, thereby increasing the volume in reservoir 38 and causing fluid to be drawn into the reservoir through catheter 36. By using the harmonic motors 74, 76 to rotate drive ring 56, and the lead screw portion 50 acting as a transmission to transfer the rotary motion into a linear motion of bellows 44, pump 22 provides bi-directional fluid flow in or out of the pump device 22 without the need for additional motors or gear systems to change the direction of fluid flow.

Efficient power coupling of primary and secondary TET coils is described in five co-pending and co-owned patent applications filed on Jun. 24, 2004, all of which are hereby incorporated by reference in their entirety, (1) "TRANSCUTANEOUS ENERGY TRANSFER PRIMARY COIL WITH A HIGH ASPECT FERRITE CORE" to J. Giordano, Daniel F. Dlugos, Jr. & William L. Hassler, Jr., Ser. No. 10/876,313; (2) "MEDICAL IMPLANT HAVING CLOSED LOOP TRANSCUTANEOUS ENERGY TRANSFER (TET) POWER TRANSFER REGULATION CIRCUITRY" to William L. Hassler, Jr., Ed Bloom, Ser. No. 10/876,038; (3) "SPATIALLY DECOUPLED TWIN SECONDARY COILS FOR OPTIMIZING TRANSCUTANEOUS ENERGY TRANSFER (TET) POWER TRANSFER CHARACTERISTICS" to Reshai Desai, William L. Hassler, Jr., Ser. No. 10/876,057; (4) "LOW FREQUENCY TRANSCUTANEOUS TELEMETRY TO IMPLANTED MEDICAL DEVICE" to William L. Hassler, Jr., Ser. No. 10/876058; and (5) "LOW FREQUENCY TRANSCUTANEOUS ENERGY TRANSFER TO IMPLANTED MEDICAL DEVICE" to William L. Hassler, Jr., Daniel F. Dlugos, Jr., Ser. No. 10/876, 307.

Figure 7:
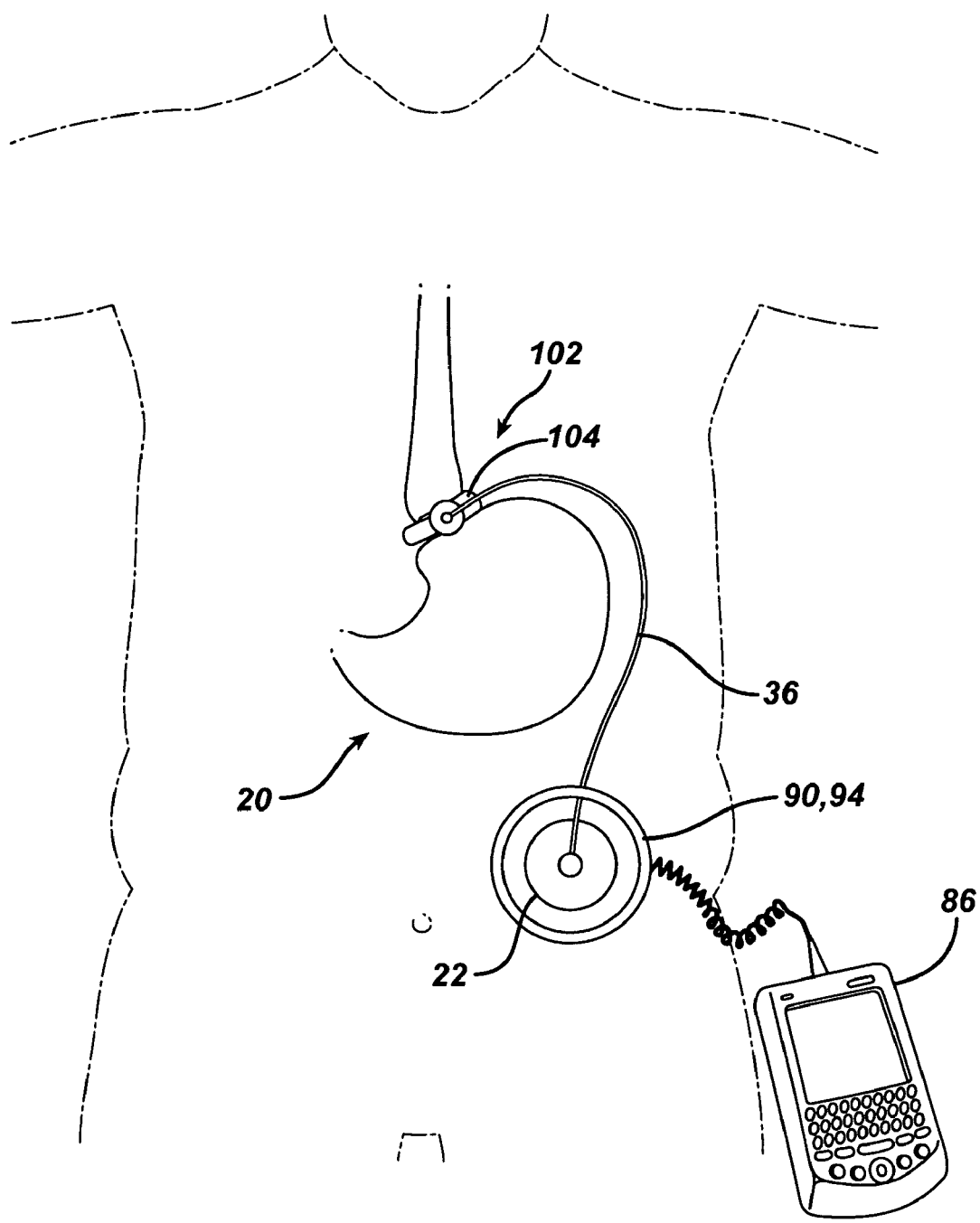
FIG. 7 is a diagrammatic view illustrating a pump and artificial sphincter implanted under a patient's skin and the volume of the sphincter being adjusted externally.

FIG. 7 illustrates an application of pumping system 20 of the present invention, in which pump device 22 is controlling fluid flow to a therapeutic device, such as an artificial sphincter 102. An artificial sphincter, such as that indicated by 102, could be utilized in any number of applications within a patient's body where it is desirable to vary the size of an orifice or organ. Depending upon the application, artificial sphincter 102 may take the form of a flexible, substantially non-extensible band containing an expandable section that is capable of retaining fluids. The expandable section would be capable of expanding or contracting, depending upon the volume of fluid contained therein. In the exemplary embodiment of FIG. 7, the expandable section of band 104 is connected to catheter 36 to enable fluid flow between the band 104 and pump device 22. The flexible material comprising band 104 enables the band 104 to be wrapped in an encircling manner about an orifice or hollow organ inside a patient's body and the two ends of the band attached against each other. While band 104 encircles the orifice or organ, the expandable section may be fully or partially filled with a fluid through catheter 36 to narrow the diameter formed by the band, and constrict the size of the orifice or organ encircled by the band. In FIG. 7, the artificial sphincter 102 is an adjustable gastric banding device that is placed around a portion of a patient's gastrointestinal (GI) system in order to restrict food intake into the system. Descriptions of gastric banding devices suitable for use in the present invention are provided in one or more of the following U.S. patents: U.S. Pat. No. 4,592,339 issued on Jun. 3, 1986 to Kuzmak et al.; U.S. Pat. No. 5,226, 429 issued on Jul. 13, 1993 to Kuzmak; U.S. Pat. No. 6,102, 922 issued on Aug. 15, 2000 to Jakobsson et al.; and U.S. Pat. No. 5,449,368 issued on Sep. 12, 1995 to Kuzmak. Each of the above-listed patents is assigned to the assignee of the present invention and is incorporated herein by reference. As shown in FIG. 7, band 104 is wrapped so as to encircle an upper portion of the patient's GI tract and create a restricted opening through the tract. While band 104 encircles the GI tract, fluid may be pumped into or out of the expandable section of the band, in order to vary the diameter of the restriction in the GI tract. FIG. 7 also illustrates an external power and control source 86 being used to control the volume of fluid in band 104. As shown in the figure, external antennas 90, 94 of device 86 are positioned over the patient's skin adjacent the location of implanted pump 22. In this position, external antennas 90, 94 transmit power and control signals to operate the pump and drive fluid in or out of band 104.

Figure 8:
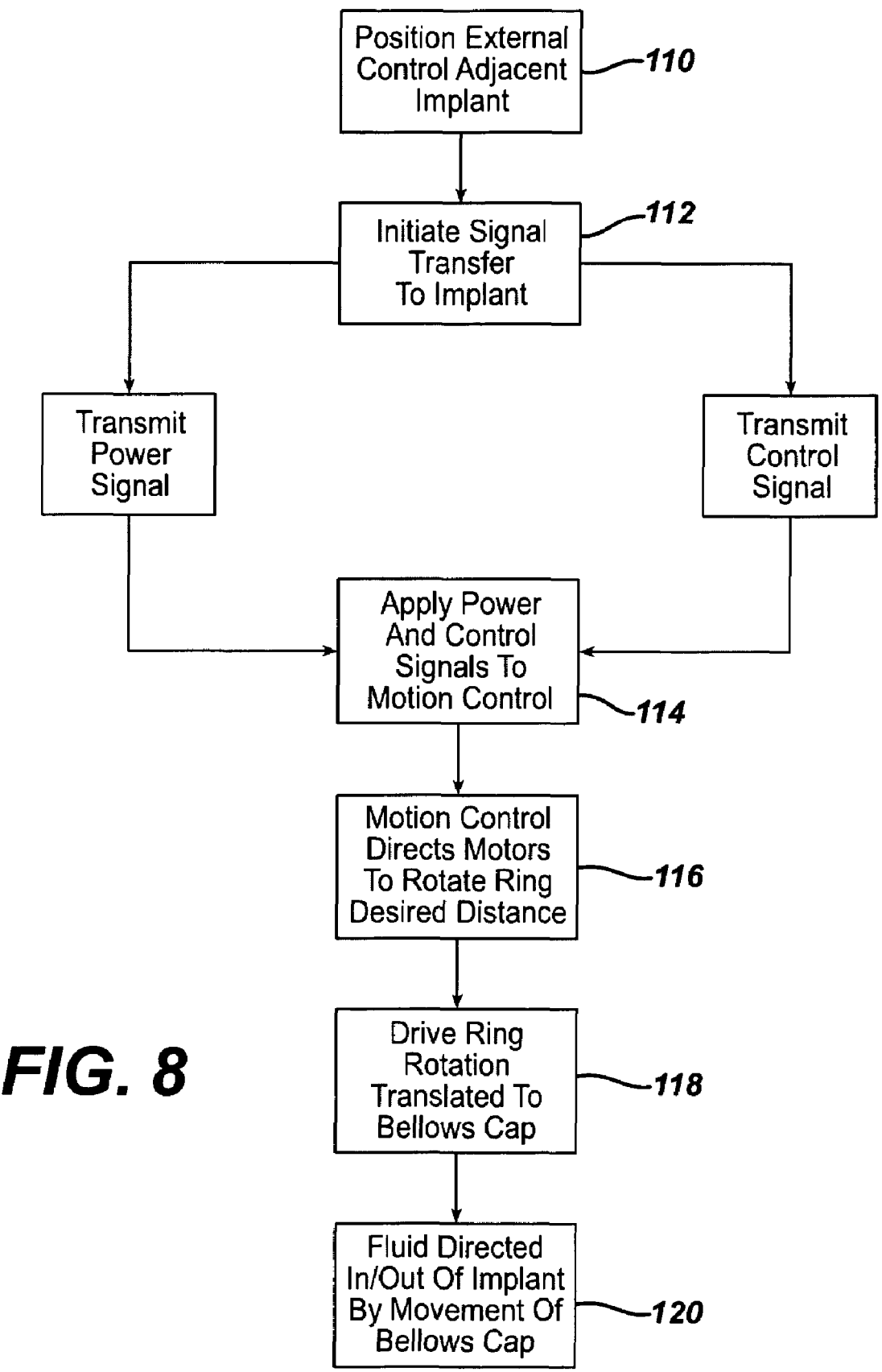
FIG. 8 is a flow diagram illustrating the method of the present invention for adjusting an artificial sphincter via an implanted pump.

FIG. 8 provides a flow diagram illustrating the operation of pump system 20 in adjusting the diameter of a therapeutic device such as artificial sphincter 102. As shown in FIG. 8, in an initial step (block 110) a sphincter adjustment is initiated by positioning external control 86 on the patient's skin adjacent to implanted pump 22. After device 86 is in place, a medical attendant directs the device to transmit RF power signal 92 to primary TET coil 90 (block 112). RF power signal 92 is received by loop antenna 66 and transmitted to internal control circuitry 100 to power on pump 22. Also during block 112, control signal 96 is transmitted by primary telemetry antenna 94 to antenna coil 68. Signal 96 includes data for directing motion control 98 to dispense (or infuse) a desired fluid volume from pump 22. In block 114, the received power and control signals are applied to motor driver 101 and motion control 98. From the data in control signal 96, motion control 98 determines the voltage to be applied to motors 74, 76, as well as the control lines across which to apply the voltage.

Motion control 98 applies a voltage signal to motors 74, 76 in block 116 to excite the piezoelectric element in each motor and cause the motor tips to vibrate against drive ring 56 and rotate the ring. Motion control 98 discontinues the voltage signal after drive ring 56 has rotated the instructed number of revolutions. While drive ring 56 is rotating, the rotary motion is transmitted through nut 52 and lead screw 50 of bellows cap 48 at block 118, so that the bellows cap is translated vertically a corresponding distance to either increase or decrease the size of bellows 44. In block 120, fluid is directed either in or out of bellows 44 as bellows cap 48 is translated. If bellows cap 48 is translated in an upward direction, the volume in bellows 44 is decreased, thereby forcing fluid from bellows 44 and into catheter 36. If bellows cap 48 is translated in a downward direction, the motion creates a vacuum within bellows 44 that draws fluid from catheter 36 into the fluid reservoir formed in the bellows. When motion control 98 discontinues the voltage signal across motors 74, 76, revolution of drive ring 56 ceases, and the fluid volumes in bellows 44, catheter 36 and sphincter 102 stabilize and remain fixed until motion control 98 is again instructed to excite the motors.

Figure 9:
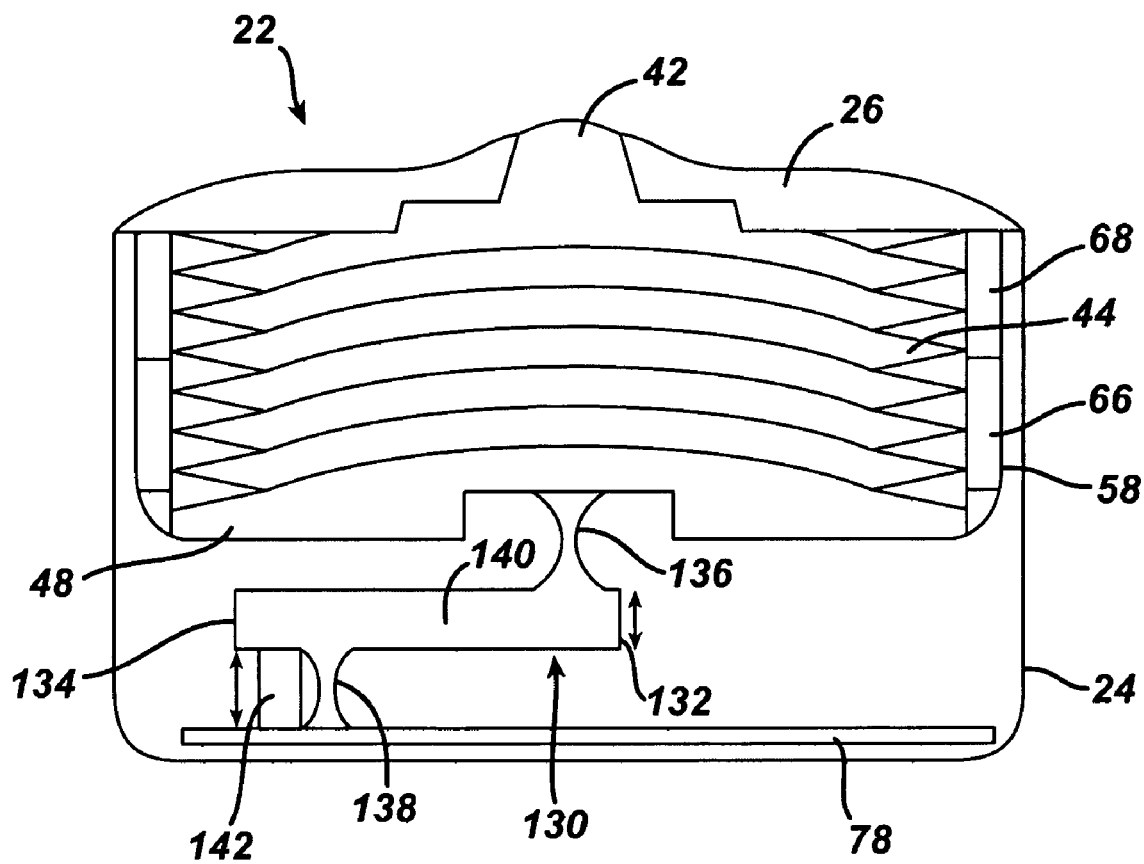
FIG. 9 is a cross-sectional view of a second embodiment for the present invention in which the bellows cap is translated by a multilayered piezoelectric actuator.

FIG. 9 provides a cross-sectional view of a second embodiment of the present invention in which bellows cap 48 is driven by a piezoelectric actuator rather than by piezoelectric motors. In this embodiment, a mechanical lever 130 replaces the rotary drive assembly formed by drive ring 56 and drive plate 54 as well as the force transmitted through nut 52 and lead screw 50. Lever 130 includes a beam 140 extending horizontally beneath bellows cap 48. An extension arm 136 extends vertically from a first end 132 of beam 140 to connect the beam 140 to the underside of bellows cap 48. A fulcrum 138 is spaced from a second end 134 of beam 140 and connects the beam 140 to control board 78. Extension arm 136 and fulcrum 138 have a narrowed, hourglass shape and are comprised of a material that enables the arm 136 and fulcrum 138 to flex mechanically in response to an applied force on beam 140.

A piezoelectric actuator 142 extends from board 78 into direct contact with beam 140 between the second beam end 134 and fulcrum 138. Actuator 142 is electrically connected to control circuitry on board 78. A motion control on board 78 is connected to actuator 142 for applying an excitation voltage to drive the actuator 142. When actuator 142 is energized, it applies a vertical force against beam 140, pulling the beam 140 downward or pushing the beam 140 upward depending upon whether the actuator 142 is increasing or decreasing in size due to the excitation. Beam 140 pivots about fulcrum 138 in response to the actuator movement due to the flexing in fulcrum 138 and arm 136. The pivoting of beam 140 amplifies the actuator movement to generate a linear force in arm 136 that lifts or lowers bellows cap 48. The length of beam 140 can vary depending upon the force required to move bellows cap 48 and the beam displacement produced by actuator 142. In this second embodiment, actuator 142 may be any type of piezoelectric actuator, such as, for example, a multi-layer piezoelectric stack actuator, a piezoelectric bimorph actuator, or a thin-layer composite-unimorph ferroelectric driver (AKA prestressed piezoelectric composite (PPC) or Thunder® actuator. Additionally, other types of piezoelectric actuators capable of moving lever 130 may also be utilized without departing from the scope of the invention.

Figure 10:
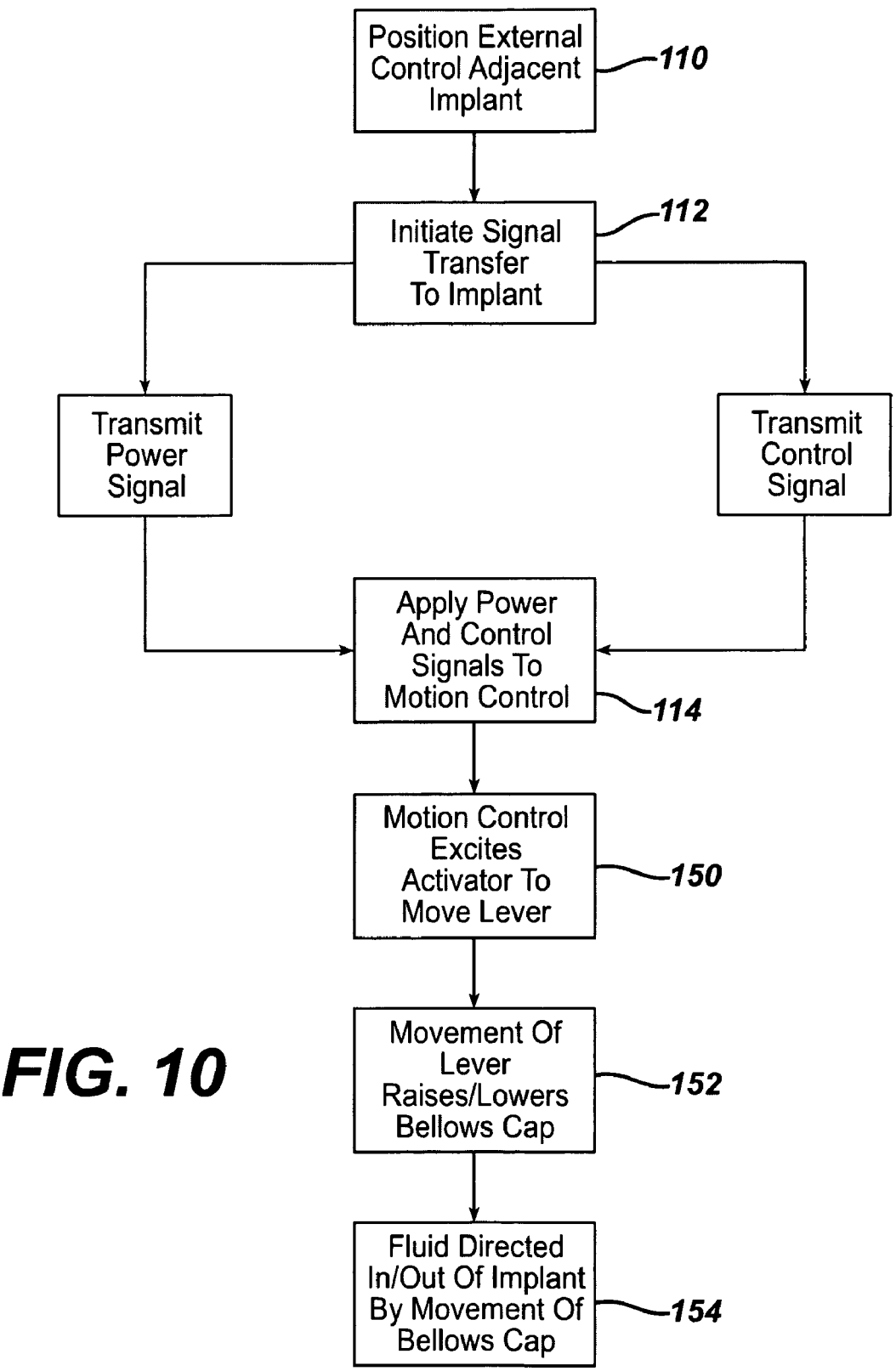
FIG. 10 is a flow diagram of a second method for adjusting an artificial sphincter via an implanted pump.

FIG. 10 provides a flow diagram for the second embodiment of the invention, in which the pump operation has been modified to utilize piezoelectric actuator 142 and mechanical lever 130 for driving bellows cap 48. The operation of the second embodiment is the same for the initial three steps of the process. Namely, external control 86 is placed adjacent to the implant 22 (block 110), signal transfer is initiated to the implant using the power and telemetry antennas 90, 94 (block 112) and the received signals 92, 96 are applied to the motion control 98 (block 114). At block 150, rather than driving motors 74, 76, motion control 98 applies a voltage to actuator 142, which moves the attached beam 140 in either an upward or a downward direction depending upon the motion of the actuator. The movement in second end 134 of beam 140 causes the beam to pivot about fulcrum 138. Because the distance between fulcrum 138 and the first end 132 of beam 140 is greater than the distance between the fulcrum and the second end 134 of the beam 140, the beam amplifies the motion of actuator 142 as the beam 140 pivots about the fulcrum 138. The amplified force is transmitted linearly through arm 136 to apply a force to move bellows cap 48 at block 152. At block 154, the upward or downward movement of bellows cap 48 either draws fluid into bellows 44 by creating a vacuum, or forces fluid from the bellows 44 by reducing the reservoir volume in the same manner as the first embodiment.

In addition to the above embodiments which couple the motor or actuator to the bellows through a mechanical amplifier transmission, bellows cap 48 may also be driven directly by a harmonic motor or harmonic actuator. In this embodiment, the harmonic motor or actuator is capable of producing sufficient actuation force and range of motion to drive the bellows cap directly from the vibrations or motions of the piezoelectric element without additional amplifying structure. The actuator is placed in direct frictional contact with the bellows cap and excited with a sufficient voltage to move the bellows cap either up or down depending upon the direction of the vibrations.

In each of the above-described embodiments, an implantable pump provides bi-directional fluid flow for use in adjusting the size of an implanted therapeutic device. The pump is driven by either piezoelectric harmonic motors or a piezoelectric actuator that is powered and controlled externally through telemetry and, accordingly, does not require a battery or any type of ferro-magnetic material as is typically necessary to drive a pump motor. Accordingly, the implantable pump can be safely used in an MRI procedure, or in a similar type of procedure that utilizes a magnetic field, without torquing or heating the pump.

While preferred embodiments of the present invention have been shown and described herein, it will be obvious to those skilled in the art that such embodiments are provided by way of example only. Numerous variations, changes, and substitutions will now occur to those skilled in the art without departing from the invention. In addition, it should be understood that every structure described above has a function and such structure can be referred to as a means for performing that function.

For example, it will become readily apparent to those skilled in the art that the above invention has equal applicability to other types of implantable bands. For example, bands are used for the treatment of fecal incontinence. One such band is described in U.S. Pat. No. 6,461,292, which is hereby incorporated herein by reference. Bands can also be used to treat urinary incontinence. One such band is described in U.S. patent application 2003/0105385, which is hereby incorporated herein by reference. Bands can also be used to treat heartburn and/or acid reflux. One such band is described in U.S. Pat. No. 6,470,892, which is hereby incorporated herein by reference. Bands can also be used to treat impotence. One such band is described in U.S. Patent Application Publ. No. 2003/0114729, which is hereby incorporated herein by reference.

As another example, while the long-term fluid integrity of a metal bellows accumulator has advantages in an adjustable artificial sphincter system, it should be appreciated that in some applications a bellows accumulator may comprise other materials. Moreover, a piston-like accumulator may be used with dynamic seals interposed between a ram and a cylinder rather than relying upon accordion-like sidewalls.

Accordingly, it is intended that the invention be limited only by the spirit and scope of the appended claims.

What is claimed is:

1. An implantable device, comprising:
   an accumulator operably configured for selective movement between a first volume and a second volume, wherein the accumulator comprises a movable portion having a movable member;
   a piezoelectric driver coupled to the accumulator and operably configured to selectively actuate the accumulator between the first volume and the second volume, wherein the piezoelectric driver is operable to drive the movable member from a first position to a second position to provide the first volume within the accumulator, wherein the piezoelectric driver is further operable to drive the movable member from the second position to the first position to provide the second volume within the accumulator;
   a controller operably configured to control the piezoelectric driver; and
   a case, wherein the accumulator includes a stationary portion coupled to the case and a movable portion, the piezoelectric driver being coupled between the case and the movable portion of the accumulator, wherein the movable portion includes a levered coupling to the case, the piezoelectric driver comprising a piezoelectric actuator coupled between the lever and the case and operably configured to impart a motion to the levered coupling.

2. The implantable device of claim 1, wherein the piezoelectric actuator comprises one selected from a group consisting of a multi-layer piezoelectric stack actuator, a piezoelectric bimorph actuator, and a prestressed piezoelectric composite.

3. The implantable device of claim 1, wherein the levered coupling comprises a beam having a first end connected to the movable portion of the accumulator and having a second end including a fulcrum connection to the case, wherein the piezoelectric actuator is connected to the second end of the beam proximate to the fulcrum connection and to the case.

4. The implantable device of claim 1, wherein the case encompasses the accumulator, the implantable device further comprising:
   a septum exteriorly exposed on the case and in fluid communication with the accumulator.

5. The implantable device of claim 1, further comprising transcutaneous energy transfer (TET) circuitry in electrical communication with the piezoelectric driver and controller.

6. The implantable device of claim 1, wherein the accumulator comprises a bellows accumulator.

* * * * *